(12) United States Patent
Schmid et al.

(10) Patent No.: US 7,053,384 B2
(45) Date of Patent: May 30, 2006

(54) REFERENCE DEVICE FOR EVALUATING THE PERFORMANCE OF A CONFOCAL LASER SCANNING MICROSCOPE, AND A METHOD AND SYSTEM FOR PERFORMING THAT EVALUATION

(75) Inventors: Karl Anton Josef Schmid, Pfaffikon (CH); Urban Georg Schnell, Muntschemier (CH)

(73) Assignee: Roche Molecular Systems, Inc., Alameda, CA (US)

(*) Notice: Subject to any disclaimer, the term of this patent is extended or adjusted under 35 U.S.C. 154(b) by 200 days.

(21) Appl. No.: 10/297,631

(22) PCT Filed: Jun. 5, 2001

(86) PCT No.: PCT/EP01/06365

§ 371 (c)(1), (2), (4) Date: Sep. 22, 2003

(87) PCT Pub. No.: WO01/94918

PCT Pub. Date: Dec. 13, 2001

(65) Prior Publication Data

US 2004/0051050 A1    Mar. 18, 2004

(30) Foreign Application Priority Data

Jun. 7, 2000    (EP)  .................................. 00810496

(51) Int. Cl.
*G01N 21/64* (2006.01)
(52) U.S. Cl. ................... 250/458.1; 250/459.1
(58) Field of Classification Search ............. 250/458.1, 250/459.1
See application file for complete search history.

(56) References Cited

U.S. PATENT DOCUMENTS

| | | | |
|---|---|---|---|
| 4,302,678 A | 11/1981 | Schiffert | ...................... 250/461 |
| 4,662,745 A | 5/1987 | Zupanick et al. | ............ 356/243 |
| 5,143,854 A | 9/1992 | Pirrung et al. | .............. 436/518 |
| 5,414,258 A | 5/1995 | Liang | ...................... 250/252.1 |
| 5,581,631 A | 12/1996 | Ortyn et al. | ................. 382/128 |
| 5,689,110 A | 11/1997 | Dietz et al. | ............... 250/252.1 |
| 5,838,435 A | 11/1998 | Sandison | .................... 356/243 |
| 6,355,919 B1 | 3/2002 | Engelhardt | ............... 250/201.3 |
| 6,472,671 B1* | 10/2002 | Montagu | ................. 250/458.1 |
| 6,635,226 B1* | 10/2003 | Tso et al. | ................... 422/129 |

FOREIGN PATENT DOCUMENTS

| | | |
|---|---|---|
| DE | 3148912 A1 | 6/1983 |
| EP | 0 497 372 A1 | 8/1992 |
| JP | 56063242 A | 5/1981 |
| JP | 04-244947 | 9/1992 |
| JP | 06-148076 | 5/1994 |
| JP | 10-010049 | 1/1998 |
| JP | 11-258512 | 9/1999 |
| WO | WO 90/15070 | 12/1990 |
| WO | WO 98/28592 | 6/1998 |
| WO | WO 99/42885 | 8/1999 |

* cited by examiner

*Primary Examiner*—Constantine Hannaher
(74) *Attorney, Agent, or Firm*—Rhea C. Nersesian; Charles M. Doyle

(57) ABSTRACT

A reference device for evaluating the performance of a confocal laser scan microscope. The reference device comprises a substrate (53) and reference fluorescing matter distributed over a surface of the substrate (53). The reference fluorescing matter has a predetermined spatial distribution over the latter surface.

10 Claims, 8 Drawing Sheets a given wavelength) by sequential pixel reading (scanning)
REFERENCE DEVICE FOR EVALUATING THE PERFORMANCE OF A CONFOCAL LASER SCANNING MICROSCOPE, AND A METHOD AND SYSTEM FOR PERFORMING THAT EVALUATION This application is a US national phase application under 35 U.S.C. 371 of international patent application PCT EP01/06365, filed Jun. 5, 2001.

FIELD OF THE INVENTION

The invention concerns a reference device for evaluating the performance of a confocal laser scan microscope of the kind used for performing a two dimensional quantitative fluorescence measurement of test matter distributed on a flat surface of a first glass substrate in particular a DNA binding array or the like, e.g. a DNA binding array of the type described in U.S. Pat. No. 5,143,854.

The invention also concerns a method for evaluating the performance of a confocal laser scan microscope of the above mentioned kind.

The invention more in particular concerns an evaluation method enabling the characterization of a confocal laser scan microscope of the above mentioned kind in terms of quantitative signal detection sensitivity, limit of detection, uniformity of the confocal volume over the scan field of view, spatial resolution of the scanning process and dynamic behavior of the measured signal over the scan field of view, said measured signal corresponding to the fluorescent light received.

The invention further concerns a system for evaluating the performance of a confocal laser scan microscope which is apt to be used for performing a two dimensional quantitative fluorescence measurement of test matter distributed on a flat surface of a substrate.

BACKGROUND

The principle of confocal laser scan microscopy for two-dimensional, quantitative fluorescence measurement is illustrated in FIGS. 1 and 2. FIG. 1 shows the optical setup of a 2-D flying spot confocal laser scan microscope, using for fluorescence excitation a laser beam 11, a dichroic beam splitter 12, a 2-dimensional scan engine 13 for spatial beam deflection in two orthogonal directions (X-Y) and a lens 14 for focusing the laser beam into an object plane 15. Fluorescent light of a longer wavelength than the excitation laser 11 is generated by exciting fluorescent molecules in the object plane 15.

Fluorescent light emitted by fluorophores located in the object plane 15 of the scanned area is collected by lens 14 and then transmitted by means of the scan engine 13 and the dichroic beam splitter 12 as a fluorescent light beam 17 which is focused by lens 18 into a pinhole aperture 19 in a conjugate plane 21 in front of a photodetection device 22.

The concept of confocal imaging, which is currently used to discriminate the generally weak fluorescence signal from background radiation, is illustrated in FIG. 2. Only optical radiation from within the confocal volume Vc, i.e., the fluorescence signal, is detected by the photodetector 22. Vc is defined by the optical transfer function of the detection optics (OTFem) and the size of the detector pinhole 19 in the conjugate plane 21. Higher background suppression rates result for smaller confocal volumes Vc.

The size of the scan field of view is typically in the order of 20×20 square millimeter. The confocal volume is generally in the order of Vc=5×5×50 cubic micrometer, where Ac=5×5 square micrometer and zc=50 micrometer is approximately the spot size and the Rayleigh range of the focused laser beam, respectively. The pixel size of the scan engine 13 for scanning the laser beam 11 in the field of view is typically 1 to 20 micrometer.

DNA binding arrays, e.g. those of the type described in U.S. Pat. No. 5,143,854, consist of a glass chip carrying a chemical system subdivided in adjacent cells, commonly called features. The features are characterized by specific probes. Specific nucleic acid sequences are immobilized (captured) by the probes and labeled with a fluorescent dye. The amount of captured nucleic acid on individual features is detected using quantitative fluorescence measurement (the fluorescent dye emits light when excited by light energy of a given wavelength) by sequential pixel reading (scanning) of the features. The features are spatially over-sampled by the scanning procedure (i.e. number of pixels>number of features) for accurate spatial referencing of the glass chip by numerical data analysis and for increased feature signal quality by averaging physically measured light intensities. Typical pixel sizes are in the order of 1 to 20 micrometer.

The ratio of the scan field of view to the cross-section Ac of the confocal volume is typically high in confocal laser scan microscopy, i.e. "scan field of view"/"cross-section Ac of the confocal volume">>1, which readily leads to a x-y position depending optical transfer function OTF(x, y)=OTFex*OTFem, where OTFex and OTFem are the optical transfer functions of the excitation and emission optics, respectively. The x-y position dependence is mainly due to mechanical misalignment and imperfections of optical and opto-mechanical components, such as e.g. the scan engine used for scanning. It causes an inhomogeneous sensitivity over the scan field of view, as schematically sketched in FIGS. 3a, 3b and 3c and this in turn leads to erroneous quantitative fluorescence measurements. As an example, FIG. 4 schematically shows the scanned image of a DNA binding array, e.g. of the type described in U.S. Pat. No. 5,143,854, which array has a chess-board pattern. As described hereinafter with reference to FIG. 4 the scanned image has a lower signal level in the top right corner, due to either inhomogeneous fluorophore density in the scanned object or inhomogeneous sensitivity of the confocal laser scan microscope over the scan field of view.

There is therefore a need for a reliable quantitative measurement and evaluation of the sensitivity over the scan field of view of a confocal laser scan microscope of the above described type.

The availability of an appropriate reference standard target object would allow to discriminate between instrument- and scanned object (e.g. a DNA binding array of the type described in U.S. Pat. No. 5,143,854) contributions to the observed non-uniformity in FIG. 4. However, no reference fluorescing target objects for characterizing key performances of a confocal laser scan microscope, i.e., sensitivity, limit of detection, uniformity-, spatial resolution- and signal dynamic behavior over the scan field of view, have been reported yet.

There is therefore a need for an appropriate reference standard target object that allows one to discriminate between instrument- and scanned object contributions to a non-uniformity of the type represented in FIG. 4.

SUMMARY OF THE INVENTION

The aim of the invention is therefore to provide a reference device, a method and a system of the above mentioned kinds that make it possible to evaluate quantitatively the performance of a confocal laser scan microscope for performing two-dimensional, quantitative fluorescence measurements.

The main advantages attained with a reference device, method, and system according to the invention are that they allow a quantitative and highly accurate evaluation of the performance of a confocal laser microscope for scanning DNA binding arrays of the above mentioned kind, and that this evaluation makes it possible to evaluate quantitatively measurement results obtained by scanning with such a microscope, e.g. a sample DNA binding array to be analyzed. In this context it is important to note that the evaluation performed according to the invention includes the measurement of the following characteristics:

a) quantitative signal detection sensitivity,
b) quantitative signal detection limit
c) uniformity of the confocal volume over the scan field of view,
d) spatial resolution of the scanning process, and
e) dynamic behavior of the measured signal over the scan field of view, said measured signal corresponding to the fluorescent light received.

BRIEF DESCRIPTION OF THE DRAWINGS

Preferred embodiments of the invention are described hereinafter with reference to the accompanying drawings wherein:

FIG. 7b shows a cross-section of the embodiment shown by FIG. 7a.

DETAILED DESCRIPTION OF THE INVENTION

The subject invention will now be described in terms of its preferred embodiments. These embodiments are set forth to aid the understanding of the invention, but are not to be construed as limiting.

Figure 1:
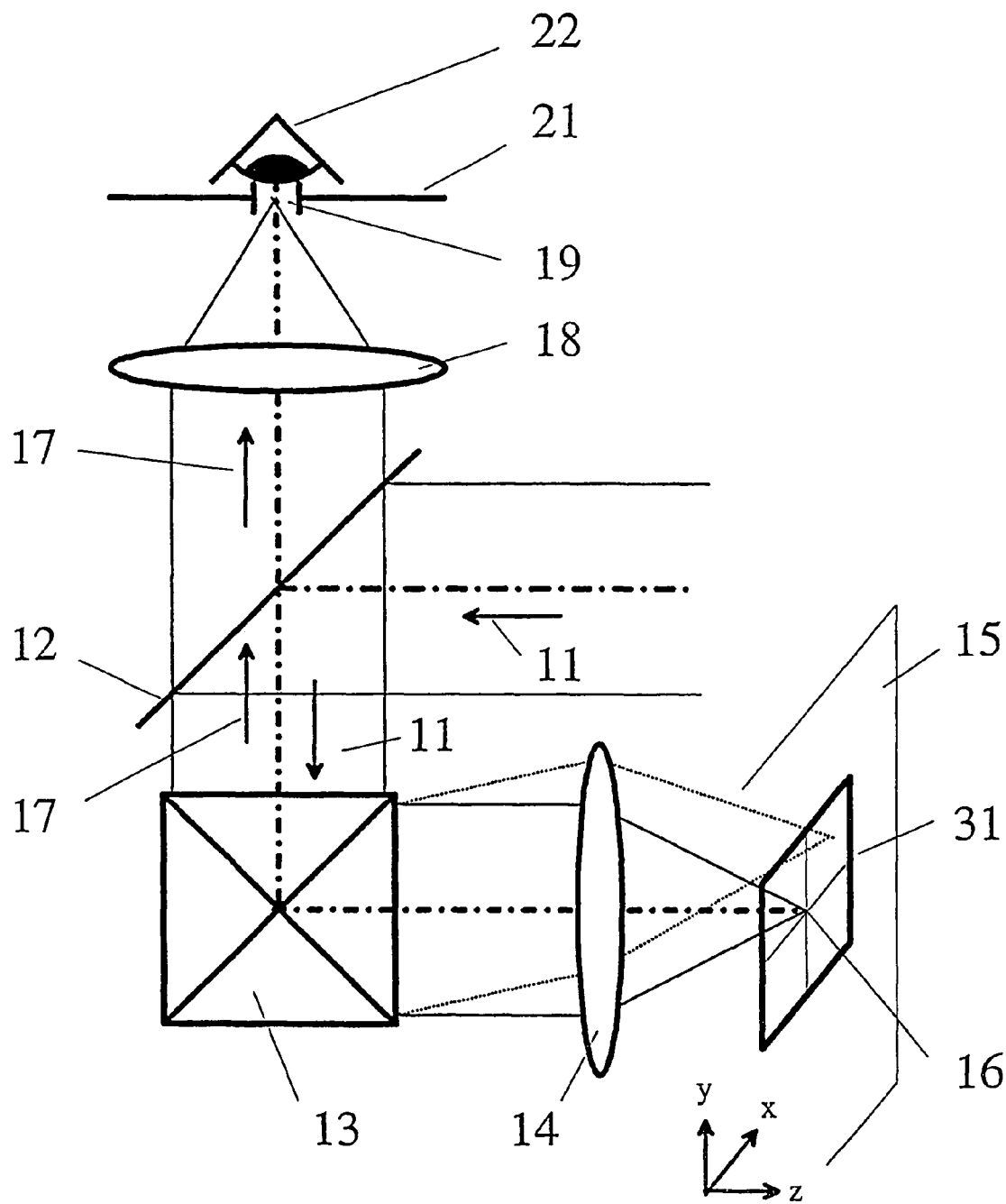
FIG. 1 shows a schematic representation of the basic setup of a confocal laser scan microscope for performing a two-dimensional, quantitative fluorescence measurement, FIG. 2 schematically shows a confocal volume Vc in an object plane.

FIG. 1 schematically shows a basic setup of a confocal laser scan microscope for two-dimensional, quantitative fluorescence measurement in case of a two-dimensional flying spot. An excitation laser beam 11, which is transmitted through a dichroic beam splitter 12 is spatially scanned by means of a two-axis scan engine 13, e.g., a galvo-scanner, in two axis X, Y, perpendicular to each other, and is focused by a lens 14 into an object plane 15 which is parallel to a X-Y-plane defined by the axis X and Y, and which is perpendicular to a third axis Z which is perpendicular to the X-Y-plane.

Fluorophores within the confocal volume Vc in the object plane 15 are excited by the focused laser spot 16 and the fluorescent light 17 generated by excitation of those fluorophores is collected and imaged by a lens 18 into a detector pinhole 19 in the conjugate plane 21 and detected by photodetector 22.

Figure 2:
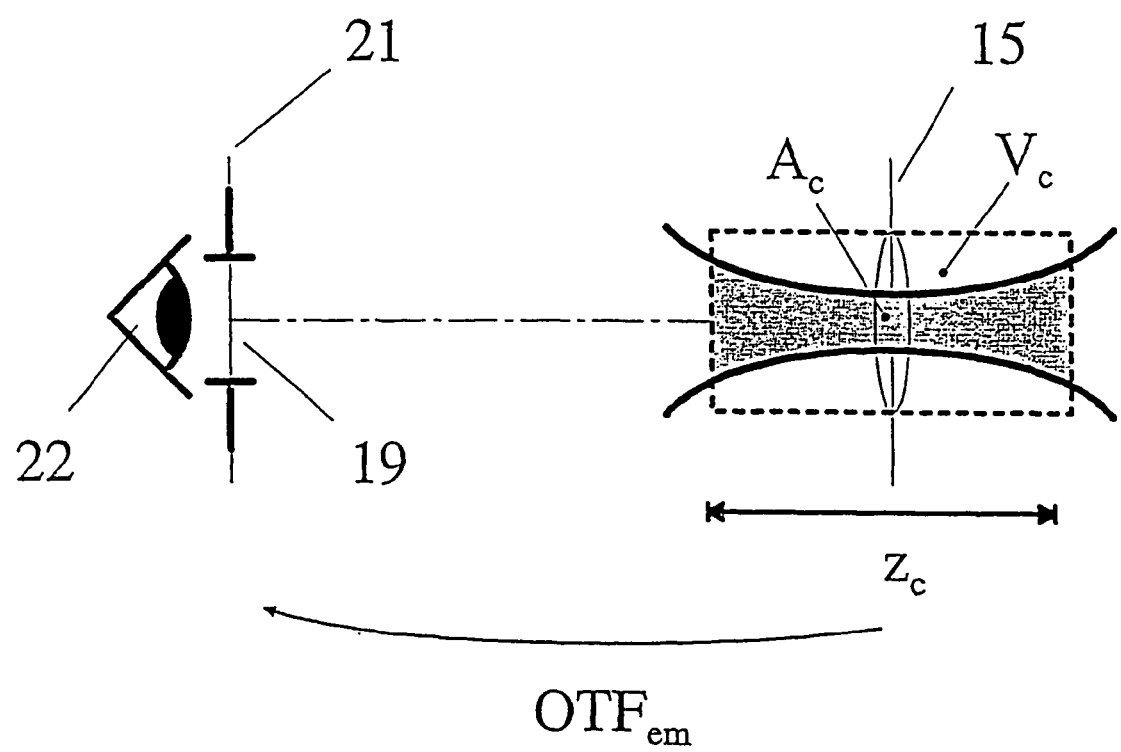

FIG. 2 schematically shows a confocal volume Vc (with Vc=Ac*zc) in the object plane 15. Confocal volume Vc is ideally a cylindrical volume having a rotation axis parallel to the Z axis and a circular cross-section. The confocal volume Vc is defined by the optical transfer function (OTFem) of the detection optics and the size and the shape of the detector pinhole 19 in the conjugate plane 21. Only optical radiation from within the confocal volume Vc is detected by the photodetector 22. The concept of confocal imaging allows high background suppression rates for detecting weak signal levels, as is commonly the case in fluorescence measurements.

Figure 3A:
FIGS. 3a, 3b and 3c show schematic representations of various forms of non-uniformity of the scanned confocal volume over the scan field of view.
Figure 3B:
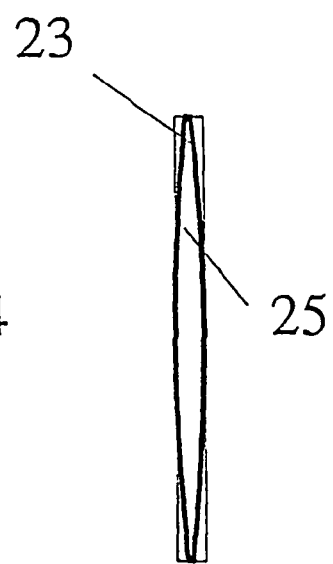
Figure 3C:
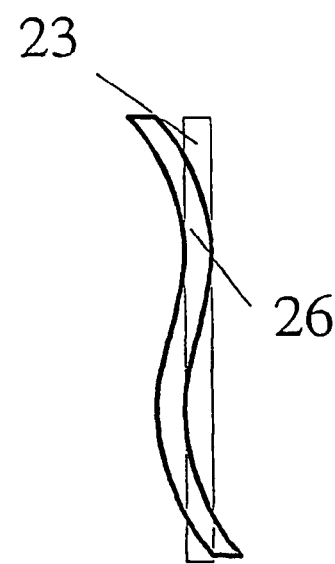

FIGS. 3a, 3b and 3c show schematic representations in the plane Y-Z of various forms of non-uniformity of the scanned confocal volume Vc, that is of deviations of the shape of this volume from the ideal shape represented in FIG. 2. These deviations cause inhomogenities of the amplitude of the fluorescent light intensity signal measured over the scanned area.

FIG. 3a shows a scanned confocal volume 24 which is tilted with respect to an ideal or nominal confocal volume 23. FIG. 3b shows a scanned confocal volume 25 which has not a constant width and which is thus non-uniform compared with the nominal confocal volume 23. FIG. 3c shows a scanned confocal volume 26 having a shape which is distorted with respect to the nominal confocal volume 23.

Mechanical misalignment and imperfection of optical and opto-mechanical components used are the main reasons for the non-uniformities of the confocal volumes represented in FIGS. 3a, 3b and 3c.

Figure 4:
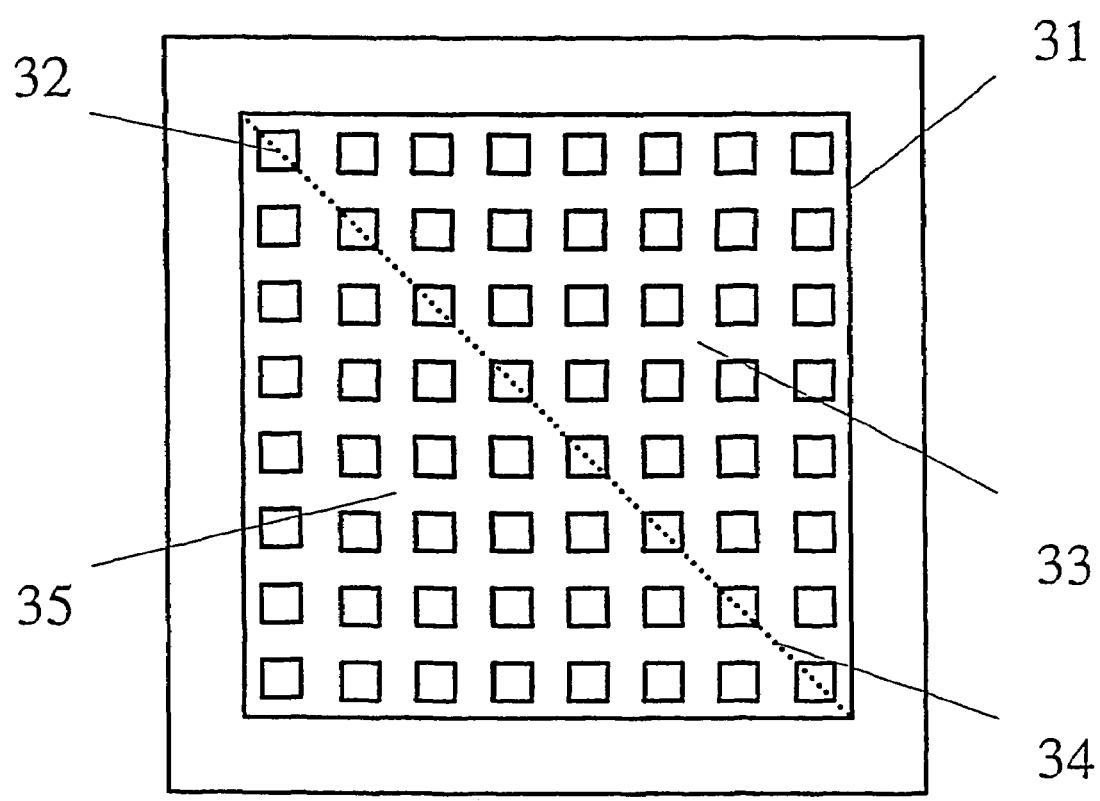
FIG. 4 shows a schematic representation of a scanned image of a DNA binding array

FIG. 4 shows a schematic representation of a scanned image of DNA binding array 31 of the type described in U.S. Pat. No. 5,143,854. Array 31 has a chess-board array of fluorescent points 32 apt to emit fluorescence light when it is irradiated with excitation light. For the purpose of the following description it is convenient to distinguish two zones of array 31: a first zone 33 which extends from a diagonal 34 to the top right corner of array 31, and a second zone 35 which extends from diagonal 34 to the low left corner of array 31. Due to either inhomogeneous fluorophore density in the scanned object or inhomogeneous sensitivity of the confocal laser scan microscope over the scan field of view, the image represented by FIG. 4 shows up that fluorescent points 32 located in zone 33 of array 31 provide fluorescent light of lower intensity than fluorescent points 32 located in zone 35. The purpose of a reference device, a method and a system according to the invention is to evaluate quantitatively to which extent such variations of the intensity of the fluorescence light detected are due specifically to inhomogeneous sensitivity of the confocal laser scan microscope over the scan field of view.

Figure 5A:
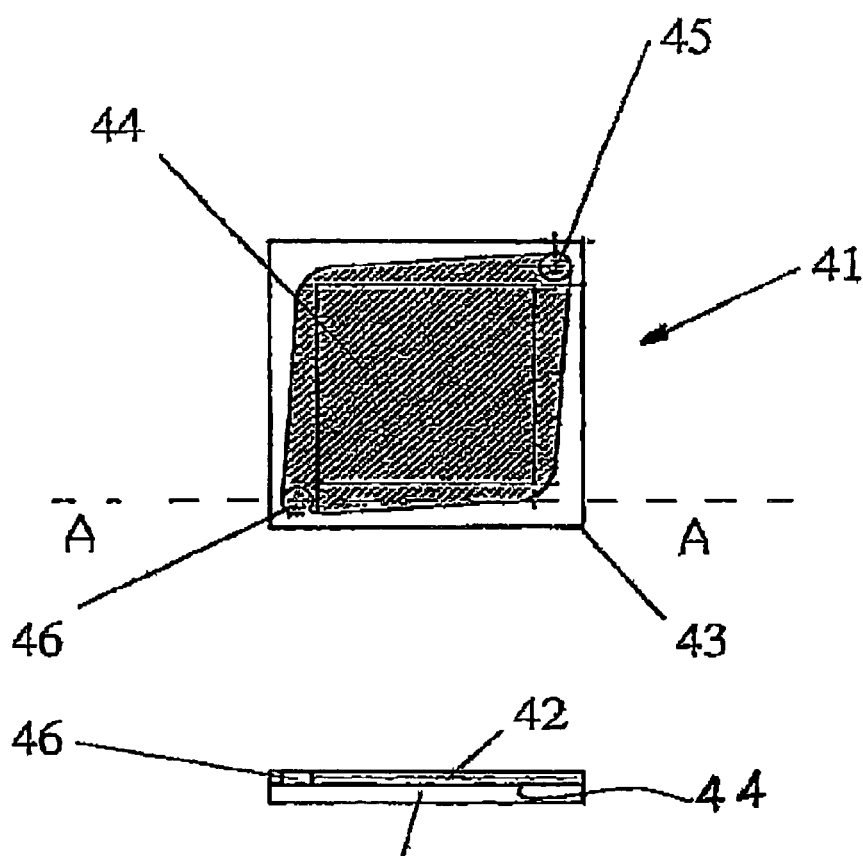
FIG. 5a shows a top view of a first embodiment of a reference device according to the invention.
Figure 5B:
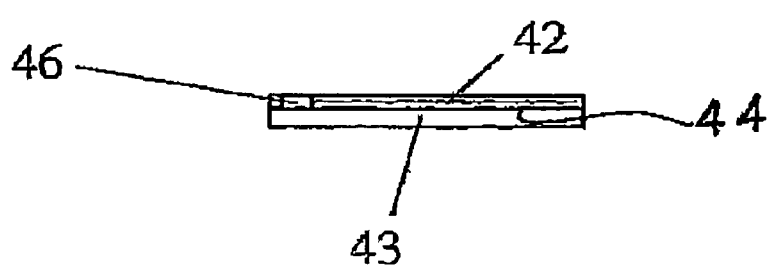
FIG. 5b shows a cross-section through a plane A—A of the embodiment shown by FIG. 5a, FIG. 6 shows the shape of a representative electrical signal obtained by measuring fluorescent light emitted by fluorescent zones located in a row of the array represented in FIGS. 5a and 5b.

FIG. 5a shows a top view and FIG. 5b a cross-section of a first embodiment of a reference device 41 according to the invention for characterizing quantitatively the homogeneity and sensitivity of a confocal laser scan microscope for two-dimensional quantitative fluorescence measurement.

The reference device 41 shown by FIGS. 5a and 5b consists of a top glass plate 42 bonded onto a glass substrate

43. The 16×16 square millimeter glass substrate 43 (thickness=1 millimeter) has a 5 micrometer etched planar cavity 44 (hatched area) which covers a surface of 11×11 square millimeters. The glass top plate 42 (thickness=0.7 millimeter) has two drilled holes 45 respectively 46 for fluid in- and outlet. Holes 45, 46 have each a diameter of 1.5 millimeter. The center of each hole 44, 45 lies at a distance of 1.38 millimeter from the edge of plate 42. In another possible embodiment, a top glass plate 42 without drilled holes 45 and 46 may not be bonded onto a glass substrate 43.

Glass substrate 43 has e.g. identical dimensions and preferably the same optical properties as the substrate of DNA binding array 31 described above with reference to FIG. 4.

The cavity 44 of the reference device is filled with dissolved fluorophores with a predetermined concentration leading to a predetermined spatial distribution of fluorophores over the scanned area. Since the fluorophores are dissolved uniformly, this spatial distribution is determined by the structure of cavity 44, and not by the dissolved fluorophores themselves. In the example described with reference to FIGS. 5a and 5b the cavity 44 is planar and therefore the spatial distribution of the fluorophores is a uniform one over the whole area of cavity 44.

Glass cover 42 of reference device 41 shown by FIGS. 5a and 5b has identical dimensions and optical properties as a glass substrate of a given DNA binding array of the type described above with reference to FIG. 4. Reference device 41 can therefore be scanned by the confocal laser scan microscope under the same optical conditions. The well defined size of the cavity and the controlled fluorophore concentration having a predetermined spatial distribution over the scanned area allows investigation of the measurement signal with respect to sensitivity (limit of detection) and homogeneity over the scan field of view. As mentioned above the spatial distribution of the dissolved fluorophores is determined by the structure of cavity 44, and not by the uniformly dissolved fluorophores themselves.

Using a solution of dissolved fluorophores has the advantage that it can be prepared just before the fluorescence measurement is performed. Thus, the reference device filled with a liquid of dissolved fluorophores is not affected by a possible bleaching effect, which otherwise could arise if it has been stored for a longer time and which could lead to a non-quantitative capability of fluorescence of the reference device over the scan field of view. In addition, various solutions with different concentrations of dissolved fluorophores can easily be prepared, which allows for fluorescence measurements at various intensity levels. In particular, it is possible to determine the limit of detectable intensity level.

The height of cavity 44 is much smaller than the depth of the confocal volume Vc given by the Rayleigh range zc, such that the thin planar layer of fluorophores in the cavity 44 allows for a reliable evaluation of e.g. possible displacements of the confocal volume Vc in the Z-direction (perpendicular to the scan field of view) as the reference device 41 is being scanned over the whole scan field of view.

Figure 6:
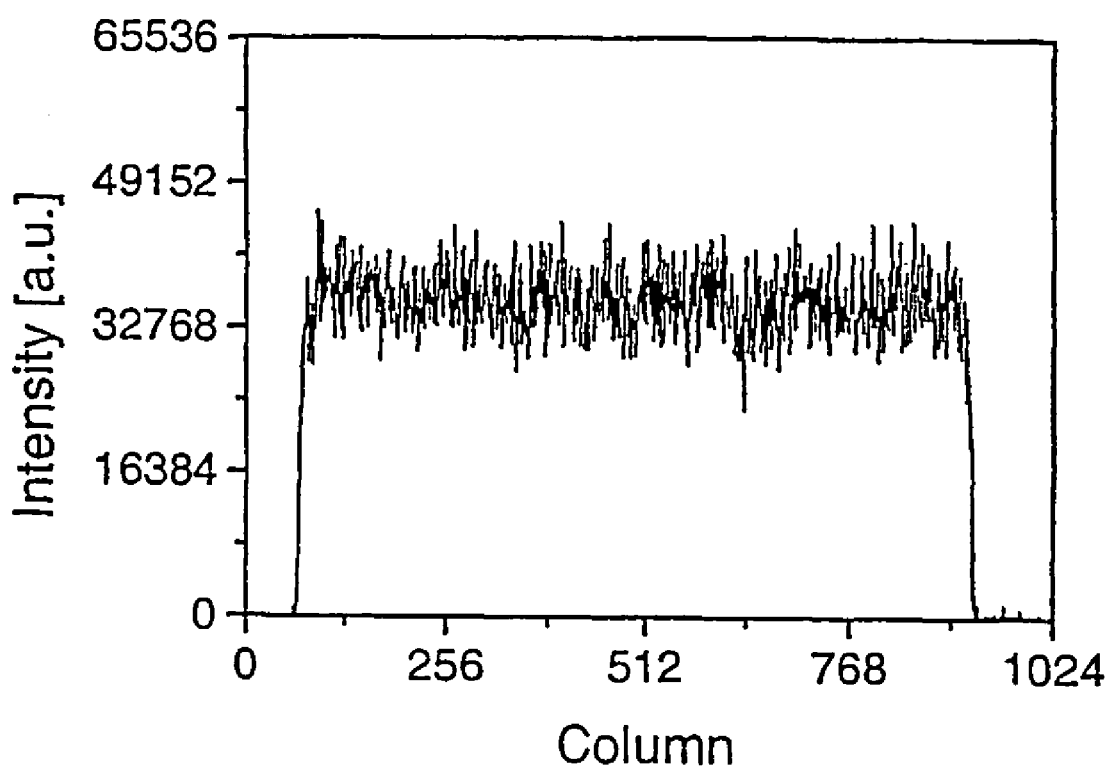

As an example FIG. 6 shows the signal profile of row 588 of 1024 of the scanned image obtained with the reference device shown by FIGS. 5a and 5b: the cavity 44 of the device has a constant thickness over its whole extension and is filled with 200 mg/ml fluorescein TRIS solution (Fluoresce in aqueous 0.1 molar TRIS buffer pH 8.3). The image can be analyzed for sensitivity and for uniformity of the confocal laser scan microscope, as shown in FIG. 6 for the line profile of row 588 of 1024 (field of view=10×10 square millimeter, pixel size=10 micrometer, the resolution of the scanning is 1024×1024 pixel, the scan time is 126 seconds, the detection sensitivity of the transimpedance amplifier used is 10 microampere per volt, the cutoff or 6 dB frequency of the low-pass filter used with the transimpedance amplifier is 30 kHz, the integration interval tdwell has a duration of 40 microseconds). As can be appreciated from FIG. 6 some noise signal is superposed on the line profile obtained. In FIG. 6 signal intensity is indicated in arbitrary units.

The deviation of the signal intensity of each pixel from a predetermined value, which is given e.g. by the signal intensity averaged over the whole scanned image, gives a quantitative parameter for the performance of a confocal laser scan microscope.

As a further application it is possible to calibrate the signal intensity level. The number of fluorophores per area can be evaluated from the concentration of dissolved fluorophores. Therefore, the signal intensity measured and the measurement sensitivity are related to the number of fluorophores per area in a quantitative manner.

Figure 7A:
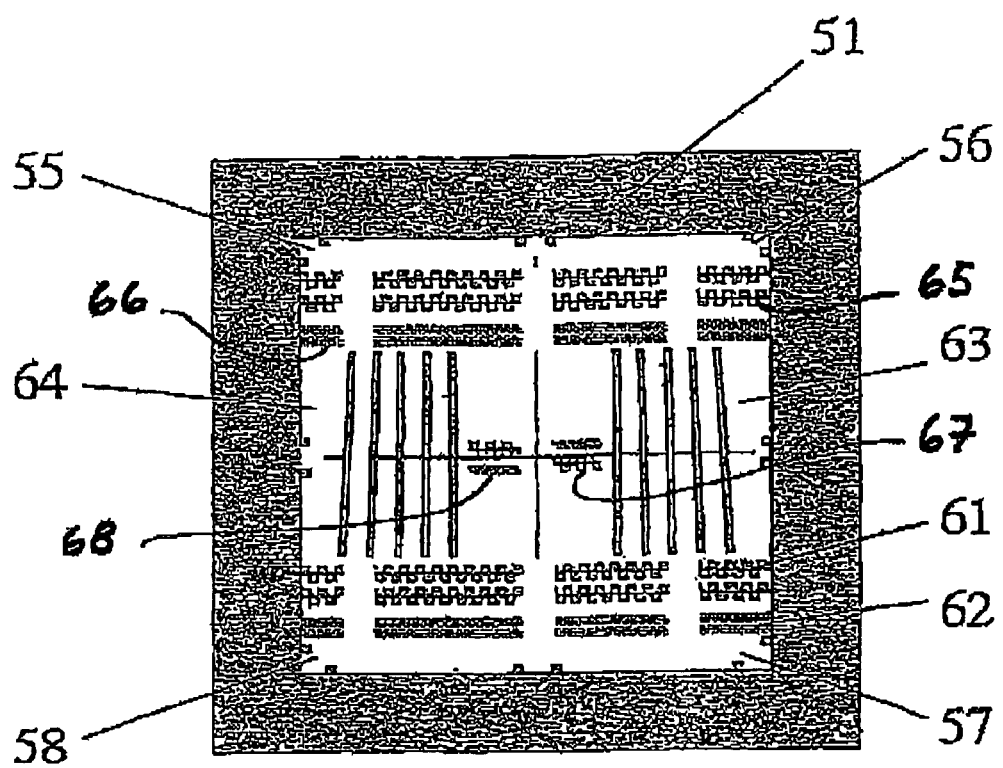
FIG. 7a shows a top view of a second embodiment of a reference device according to the invention.
Figure 7B:
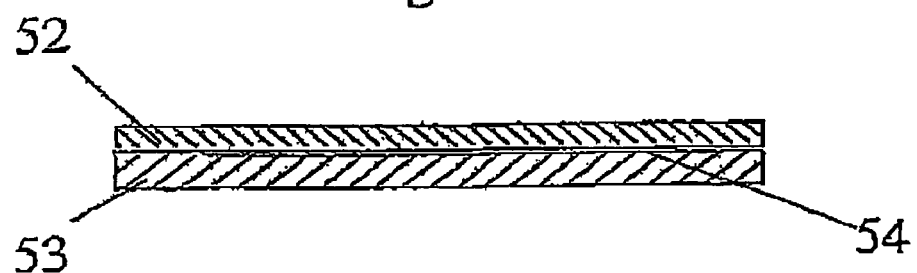
Figure 7C:
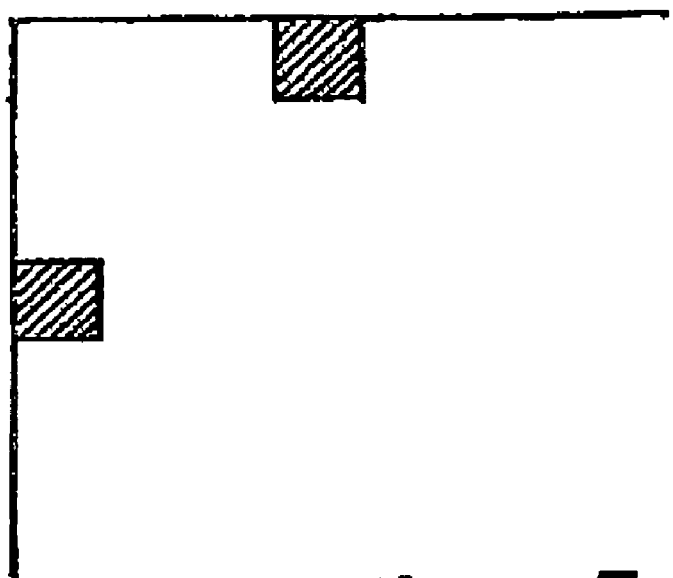
Figure 7D:
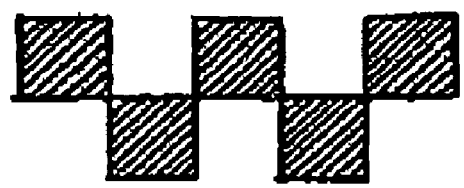

FIG. 7a shows a top view and FIG. 7b a cross-section of a second embodiment of a reference device according to the invention for a quantitative evaluation of the homogeneity and spatial resolution of a confocal laser scan microscope. FIG. 7c represents an enlarged view of FIG. 7a corner zone 55. FIG. 7d represents an enlarged view oft portion of FIG. 7a fluorescent zone 61 or 62.

In FIG. 7a some dimensions in micrometer are indicated. In FIG. 7b some dimensions in millimeters are indicated.

The reference device 51 shown by FIGS. 7a and 7b consists of a top glass plate 52 (thickness =0.7 millimeter) on a glass substrate 53 having an area of 16×16 square millimeter. The upper surface of glass substrate 53 (thickness 1 millimeter) has a 5 micrometer etched, microstructured depression forming a cavity 54 having a bottom inner surface. Cavity 54 is filled with uniformly dissolved fluorophores having a predetermined concentration, which leads to a predetermined spatial distribution of fluorescent zones over the area of cavity 54. This spatial distribution is not determined by the uniformly dissolved fluorophores themselves, but by the structure of cavity 54. Cavity 54 is covered by the glass top plate 52 which has a lower outer surface. The space comprised between the lower outer surface of plate 52 and the bottom inner surface of depression 54 has a thickness D which varies according to a predetermined function of the form D=f(x,y) over the entire area of depression 54. The latter space is at least partially filled with dissolved fluorophores.

Glass substrate 53 has e.g. identical dimensions and preferably the same optical properties as the substrate of DNA binding array 31 described above with reference to FIG. 4.

Glass cover 52 of reference device 51 has identical optical properties as a glass substrate of a given DNA binding array 31 of the kind described above with reference to FIG. 4. Reference device 51 can therefore be scanned by a confocal laser scan microscope under the same optical conditions.

The microstructured cavity 54 comprises different patterns of fluorescent zones. In FIG. 7a each non-fluorescent zone is represented by a shaded surface.

A first pattern of fluorescent zones comprises just two non-fluorescent zones each represented in FIG. 7a by a shaded square. In FIG. 7a fluorescent zones having this first pattern are located at each of the corner zones 55, 56, 57, 58 of reference device 51. The measured signals corresponding to the intensity of fluorescent light emitted from these corner zones are evaluated in order to assess the degree of uniformity over the scan field of view of the scanning performed with a confocal laser scan microscope. FIG. 7c represents an enlarged view of FIG. 7a corner zone 55. The first pattern of fluorescent zones comprises non-fluorescent zones represented each by a shaded square and a fluorescent zone surrounding those squares.

Zones 61 and 62 located at different rows of reference device 51 have a second pattern of spatial distribution of fluorescent features. The measured signals corresponding to fluorescent light emitted from zones like 61 and 62 are evaluated in order to assess the resolution of the scanning performed with a confocal laser scan microscope. In addition, since the dimensions of the zones 61 and 62 are known, the accuracy of the scan steps performed by the scanning engine can be assessed. Zone 61 has a dimension d1=20 micrometer. Zone 62 has a dimension d2=10 micrometer. As shown in FIG. 7a the zones 61 and 62 are subdivided such that the cavity forms one connected reservoir which is filled by the dissolved fluorophores. FIG. 7d represents an enlarged view of a portion of fluorescent zone 61 or 62. As shown by FIG. 7d each pattern of fluorescent zone 61 or 62 comprises non-fluorescent zones (microstructures) represented by shaded squares and a fluorescent zone surrounding those squares. Also represented in FIG. 7a are patterns of fluorescent zones similar to patterns of zone 61 and 62; these similar patterns are designated in FIG. 7a as 65, 66, 67 and 68.

Zones 63, 64 represented on FIG. 7a having the appearance of a group of bars having different inclination angles with respect to the vertical line in the center of FIG. 7a represent a third pattern of fluorescent features available on reference device 51. As shown on FIG. 7a each pattern of fluorescent zones 63, 64 comprise non-fluorescent zone represented by shaded bars (microstructures) and a fluorescent zone surrounding those bars. The measured signals corresponding to fluorescent light emitted from a zone like zone 63 is evaluated in order to assess the dynamic signal behavior associated to the scanning performed with a confocal laser scan microscope.

The present invention relates to the reference devices described above and shown in FIGS. 5a, 5b and 7a, 7b respectively, which are used for a quantitative evaluation of a confocal laser scan microscope for two-dimensional, quantitative fluorescence measurement. Typical characteristics determined with a reference device, respectively a method, according to the invention are a) quantitative signal detection sensitivity,
b) quantitative signal detection limit,
c) uniformity of the confocal volume over the scan field of view,
d) spatial resolution of the scanning process, and
e) dynamic behavior of the measured signal over the scan field of view, said measured signal corresponding to the fluorescent light received.

The above mentioned use of the invention for evaluating the performance of a confocal laser scan microscope substantially comprises scanning a reference device according to the invention with a microscope to be evaluated in order to obtain a first set of measurement values,
processing said first set of measurement values in order to obtain correction factors,
storing said correction factors,
scanning a sample, e.g. a DNA binding array, with the evaluated microscope in order to obtain a second set of measurement values, and
correcting said second set of measurement values with said correction factors in order to obtain a third set of values which are free from deviations due to the performance of the scanner and which therefore more accurately correspond to characteristics of the particular sample examined.

Although preferred embodiments of the invention have been described above using specific terms, such description is for illustrative purposes only, and it is to be understood that changes and variations may be made without departing from the spirit or scope of the claims of this patent application.

List of reference numbers

| | |
|---|---|
| 11 | excitation laser beam |
| 12 | dichroic beam splitter |
| 13 | two-axis scan engine |
| 14 | lens |
| 15 | object plane |
| 16 | focused laser spot |
| 17 | fluorescent light |
| 18 | lens |
| 19 | detector pinhole |
| 21 | conjugate plane |
| 22 | photodetector |
| 23 | nominal confocal volume (cross-section in plane z-y) |
| 24 | scanned confocal volume (cross-section in plane z-y) |
| 25 | scanned confocal volume (cross-section in plane z-y) |
| 26 | scanned confocal volume (cross-section in plane z-y) |
| 31 | DNA binding array (located in object plane) |
| 32 | fluorescent point or fluorescent feature |
| 33 | zone |
| 34 | diagonal |
| 35 | zone |
| 41 | first embodiment of reference device |
| 42 | top plate |
| 43 | bottom plate |
| 44 | cavity |
| 45 | hole |
| 46 | hole |
| 51 | second embodiment of reference device |
| 52 | top plate |
| 53 | bottom plate |
| 54 | cavity |
| 55 | zone having a first pattern of fluorescent features |
| 56 | zone having a first pattern of fluorescent features |
| 57 | zone having a first pattern of fluorescent features |
| 58 | zone having a first pattern of fluorescent features |
| 61 | zone having a second pattern of fluorescent features |
| 62 | zone having a second pattern of fluorescent features |
| 63 | zone having a third pattern of fluorescent features |
| 64 | zone having a third pattern of fluorescent features |
| 65 | zone having a pattern of fluorescent features similar to 61 and 62 |
| 66 | zone having a pattern of fluorescent features similar to 61 and 62 |
| 67 | zone having a pattern of fluorescent features similar to 61 and 62 |
| 68 | zone having a pattern of fluorescent features similar to 61 and 62 |

65 zone having a pattern of fluorescent features similar to 61 and 62

66 zone having a pattern of fluorescent features similar to 61 and 62

67 zone having a pattern of fluorescent features similar to 61 and 62

68 zone having a pattern of fluorescent features similar to 61 and 62

The invention claimed is:

1. A reference device for evaluating the performance of a confocal laser scan microscope, comprising:
a substrate; and reference fluorescent matter distributed over a surface of said substrate, said reference fluorescent matter having a predetermined spatial distribution over said surface, and said reference fluorescent matter being dissolved in a liquid in a predetermined concentration.

2. A reference device according to claim 1, wherein said reference fluorescent matter has a constant thickness over said surface of said substrate.

3. A reference device according to claim 1, wherein said reference fluorescent matter has a thickness which is less than a depth (zc) of a confocal volume (Vc) of said confocal laser scan microscope.

4. A reference device according to claim 1, wherein said reference fluorescent matter is uniformly distributed over said surface of said substrate, and said reference fluorescent matter has a predetermined concentration.

5. A reference device according to claim 1, wherein:
said substrate has an upper surface having a depression, said depression having a constant thickness and extending over a substantial portion of said upper surface, said depression further having an inner surface on a bottom of said depression; and
a cover plate, said cover plate being optically transparent and covering said depression of said substrate:
said cover plate further having a lower outer surface and being arranged so that a space between said lower outer surface and said bottom inner surface of said depression has a constant thickness over the entire area of said depression;
one or more zones within said space being completely filled with said reference fluorescent matter extending over the entire thickness of each zone.

6. A method for evaluating the performance of a confocal laser scan microscope; of the kind used for performing a two-dimensional quantitative fluorescence measurement of test matter distributed on a flat surface of a first substrate, said method comprising:
performing a two-dimensional quantitative fluorescence measurement of a reference device using said microscope to obtain measured values for one or more quantitative parameters, said reference device comprising a second substrate and reference fluorescent matter distributed over a surface of said second substrate, said reference fluorescent matter having a predetermined spatial distribution over said surface, and said reference fluorescent matter being dissolved in a liquid in a predetermined concentration.

7. The method of claim 6, said method further comprising processing said measured values and predetermined values for determining a quantitative parameter of the performance of said microscope.

8. The method of claim 6, wherein said substrate has an upper surface having a depression, said depression having a constant thickness and extending over a substantial portion of said upper surface, said depression further having an inner surface on a bottom of said depression; and a cover plate, said cover plate being optically transparent and covering said depression of said substrate;
said cover plate further having a lower outer surface and being arranged so that a space between said lower outer surface and said bottom inner surface of said depression has a constant thickness over the entire area of said depression;
one or more zones within said space being completely filled with said reference fluorescent matter extending over the entire thickness of each zone.

9. A method according to claim 6, wherein said two-dimensional quantitative fluorescence measurement is effective for use with a DNA binding array.

10. A system for evaluating the performance of a confocal laser scan microscope, comprising:
a confocal laser scan microscope, and
a reference device for evaluating the performance of a confocal laser scan microscope, said reference device including a substrate and reference fluorescent matter distributed over a surface of said substrate, said reference fluorescent matter having a predetermined spatial distribution over said surface, and said reference fluorescent matter being dissolved in a liquid in a predetermined concentration.

* * * * *